US012766305B2

(12) United States Patent
Kawaguchi et al.

(10) Patent No.: US 12,766,305 B2
(45) Date of Patent: Oct. 20, 2026

(54) CLAMP

(71) Applicant: TERUMO KABUSHIKI KAISHA, Tokyo (JP)

(72) Inventors: Satoshi Kawaguchi, Shizuoka (JP); Masahiro Akiyama, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 962 days.

(21) Appl. No.: 17/970,373

(22) Filed: Oct. 20, 2022

(65) Prior Publication Data

US 2023/0037368 A1 Feb. 9, 2023

Related U.S. Application Data

(63) Continuation of application No. PCT/JP2021/017192, filed on Apr. 30, 2021.

(30) Foreign Application Priority Data

May 11, 2020 (JP) ................................ 2020-083050

(51) Int. Cl.
*A61M 39/28* (2006.01)

(52) U.S. Cl.
CPC ................................ *A61M 39/286* (2013.01)

(58) Field of Classification Search
CPC .......... A61B 1/00135; A61M 5/16881; A61M 39/28; A61M 39/284; A61M 39/286
USPC .......................................................... 604/250
See application file for complete search history.

(56) References Cited

U.S. PATENT DOCUMENTS

2010/0249510 A1* 9/2010 Yamada ............ A61B 1/00135 600/121
2013/0310768 A1 11/2013 Ebara et al.
2017/0326294 A1* 11/2017 Kato ........................ F16B 2/10

FOREIGN PATENT DOCUMENTS

JP 2001-259030 A 9/2001
JP 2003-235971 A 8/2003
JP 2010-125088 A 6/2010
JP 2013-176543 A 9/2013
JP 2018-000836 A 1/2018

(Continued)

OTHER PUBLICATIONS

International Search Report for International Application No. PCT/JP2021/017192, mailed Jul. 6, 2021.

(Continued)

*Primary Examiner* — Philip E Stimpert
(74) *Attorney, Agent, or Firm* — Sheridan Ross PC

(57) ABSTRACT

A clamp includes a fixed portion including an upper portion on which a medical tube is to be placed; a movable portion that faces the fixed portion; a curved portion that connects the fixed portion and the movable portion and is configured to elastically deform; a pressing portion that protrudes from the movable portion toward the fixed portion, and presses and closes the medical tube; a pair of sidewalls that protrude from both side portions of the fixed portion in a wall shape, respectively, and are configured to prevent lateral displacement of the medical tube; and a standing portion that faces the curved portion. The standing portion is provided with a lateral displacement prevention mechanism that prevents sideward deformation of the movable portion when the movable portion is pressed.

20 Claims, 7 Drawing Sheets

(56) References Cited

FOREIGN PATENT DOCUMENTS

| | | | |
|---|---|---|---|
| WO | WO 2012/111310 | A1 | 8/2012 |
| WO | WO 2016/125820 | A1 | 8/2016 |

OTHER PUBLICATIONS

Written Opinion for International Application No. PCT/JP2021/017192, mailed Jul. 6, 2021.
Machine Translation of Official Action for Japan Patent Application No. 2022-521842, dated Jul. 9, 2024, 5 pages.
International Preliminary Report on Patentability for International Application No. PCT/JP2021/017192, mailed Nov. 24, 2022.

* cited by examiner

CLAMP

CROSS-REFERENCE TO RELATED APPLICATIONS

The present disclosure is a continuation of and claims benefit to PCT/JP2021/017192 filed on Apr. 30, 2021, entitled "CLAMP" which claims priority to Japanese Patent Application No. 2020-083050 filed on May 11, 2020. The entire disclosures of the applications listed above are hereby incorporated herein by reference, in their entireties, for all that they teach and for all purposes.

BACKGROUND

The present disclosure relates to a clamp for closing a flexible tube.

Medical tubes are typically used to provide a flow path (e.g., a fluid flow path) when connected to a blood bag and the like of a blood sampling set or a flow path when connected to a bag and the like of an infusion set. A clamp is attached to these medical tubes to close the flow path.

The clamp generally includes a hole portion through which the medical tube is inserted, a pressing portion that presses and closes the inserted medical tube, a movable portion for inputting an operation force to the pressing portion, and a lock mechanism that maintains the movable portion in a pressed state. In an initial state of the clamp, the pressing portion is opened, or maintained in an open state, with an elastic force of the movable portion. When a user presses the movable portion (e.g., against the elastic force), the pressing portion closes the tube, and the movable portion is locked by the lock mechanism.

In a blood center or the like, for example, that processes a large number of blood bags, the user may continuously perform an operation of closing a large number of clamps. In addition, in a busy medical site, the user may perform an operation of quickly closing a clamp. In such a case, the user may operate the clamp with one hand without visually checking the vicinity of the hand. In a rare cases, the medical tube may be pressed by the clamp into a state of being laterally displaced from the pressing portion, resulting in an incomplete closure of the flow path of the medical tube.

In order to prevent such incomplete closures of the flow path of a medical tube, Japanese Patent Application No. 2018-000836 A discloses a technique for preventing lateral displacement of a medical tube by providing a pair of sidewalls on both side portions of a pressing portion.

BRIEF SUMMARY

However, in the above clamp, it is found that a new problem occurs in that a movable portion may be locked by a lock mechanism while the pressing portion rides on the sidewalls, and the pressing portion may not completely close the medical tube. As can be appreciated, this incomplete closure can allow fluid to flow through the medical tube when a restriction of fluid flow may be required for safe operation.

Therefore, an object of the present disclosure is to provide a clamp that is capable of reliably closing a medical tube. Stated another way, the present disclosure provides a clamp that can selectively and reliably open and close a fluid flow path of a medical tube.

One aspect of the present disclosure is a clamp, including: a fixed portion including an upper portion on which a tube is to be placed; a movable portion that faces the fixed portion and is above the fixed portion; a curved portion that is curved from one end of the fixed portion, extends upward, is connected to one end of the movable portion, and supports the movable portion so as to make the movable portion displaceable in an up-down direction of the fixed portion with elastic deformation; a pressing portion that protrudes from the movable portion toward the fixed portion, and presses and closes the tube when the movable portion is pressed; a pair of sidewalls that protrude from both side portions of the fixed portion in a wall shape, respectively, and are configured to prevent lateral displacement of the tube; and a standing portion that extends upward from the other end of the fixed portion, faces the curved portion, and is provided with a lock mechanism configured to maintain the movable portion in a pressed state, in which the standing portion includes a lateral displacement prevention mechanism that prevents sideward deformation of the movable portion when the movable portion is pressed.

According to the clamp described herein, the lateral displacement prevention mechanism prevents the lateral displacement of the movable portion, and thus it is possible to prevent an event in which the pressing portion rides on the sidewalls and thereby ensure that the medical tube is reliably closed by the clamp.

The preceding is a simplified summary of the disclosure to provide an understanding of some aspects of the disclosure. This summary is neither an extensive nor an exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more features set for above or described in detail below.

Numerous additional features and advantages are described herein and will be apparent to those skill in the art upon consideration of the following Detailed Description and in view of the figures.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
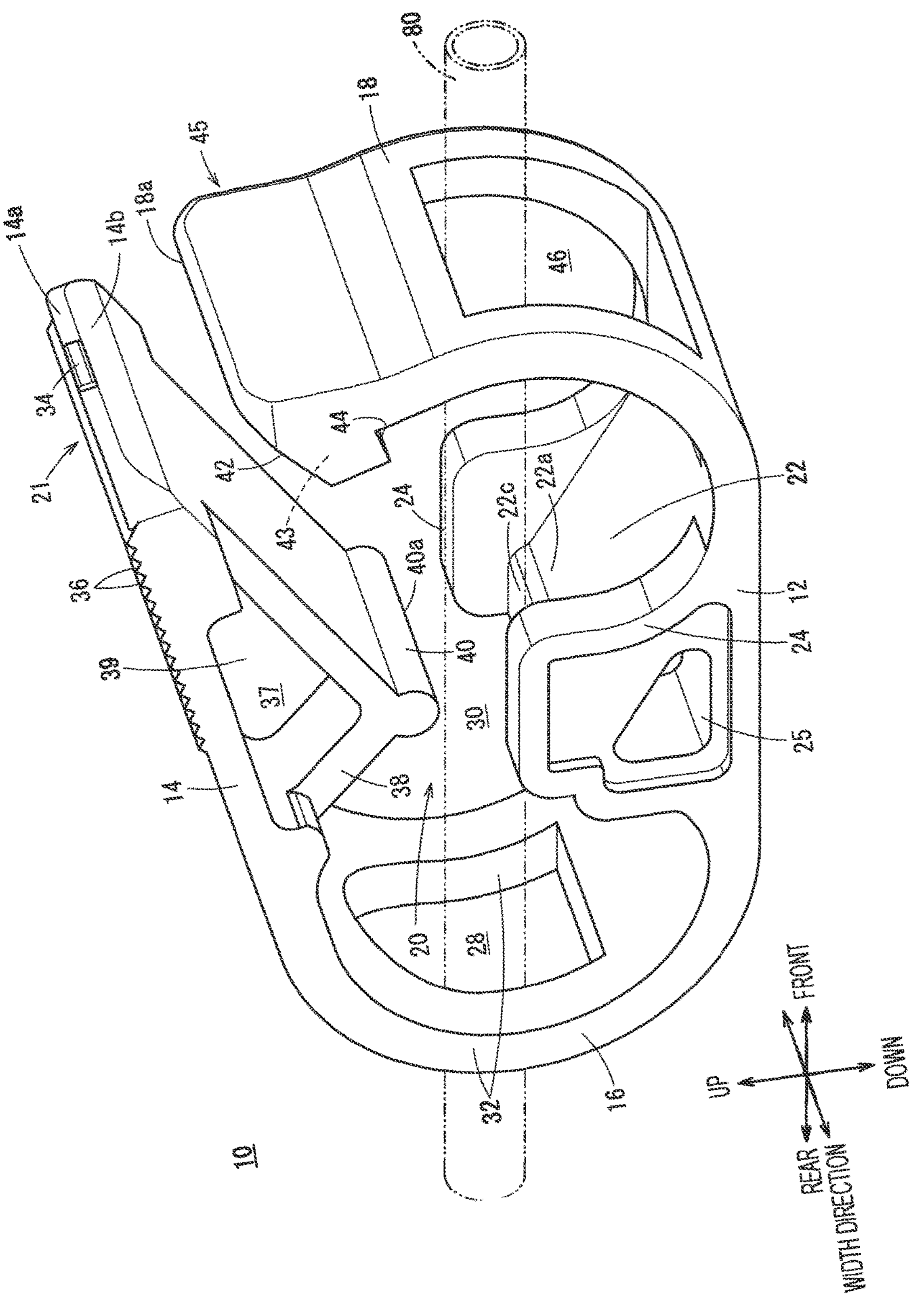
FIG. 1 is a first perspective view of a clamp according to at least one embodiment of the present disclosure.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of “including,” “comprising,” or “having” and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by “for example,” “by way of example,” “e.g.,” “such as,” or similar language) is not intended to and does not limit the scope of the present disclosure.

The ensuing description provides embodiments only, and is not intended to limit the scope, applicability, or configuration of the claims. Rather, the ensuing description will provide those skilled in the art with an enabling description for implementing the described embodiments. It being understood that various changes may be made in the function and arrangement of elements without departing from the spirit and scope of the appended claims.

It is with respect to the above issues and other problems that the embodiments presented herein were contemplated.

Hereinafter, embodiments of a clamp will be described in detail with reference to the accompanying drawings.

A clamp 10 according to at least one embodiment of the present disclosure is illustrated in FIG. 1. The clamp 10 may be integrally formed of an elastically deformable material such as a resin material. The clamp 10 is used for an operation such as selectively closing and opening a medical tube 80 (e.g., closing and opening a fluid flow path of the medical tube 80, etc.) such as a blood tube or an infusion tube by being attached to the medical tube 80.

The clamp 10 according to at least one embodiment of the present disclosure includes a fixed portion 12 on which the medical tube 80 is to be placed, a movable portion 14 disposed to face an upper side of the fixed portion 12, a curved portion 16 connecting the fixed portion 12 and the movable portion 14, a standing portion 18 facing the curved portion 16, a closing portion 20 for closing the medical tube 80, and a lateral displacement prevention mechanism 21 that prevents lateral displacement of the movable portion 14.

The fixed portion 12 may correspond to a plate-like portion extending along a plane arranged in a front-rear direction (e.g., an insertion direction of the medical tube 80), and includes an upper portion on which the medical tube 80 is to be placed. The curved portion 16 may extend from a rear, or back, end portion of the fixed portion 12 toward the upper side of the fixed portion 12. In addition, the standing portion 18 extends from a front end portion of the fixed portion 12 toward the upper side of the fixed portion 12. A base portion 22 constituting a part of the closing portion 20 and a pair of sidewalls 24 extending from both side portions of the fixed portion 12 in a width direction toward the upper side, respectively, are formed at a center portion in the front-rear direction of the fixed portion 12.

The curved portion 16 is a member extending from the fixed portion 12 toward the upper side, and is curved in a semicircular shape in a side view. The curved portion 16 can be elastically deformed in a direction of decreasing or increasing a radius of curvature. A first insertion hole 28, or first aperture, that penetrates or passes through in a thickness direction (the front-rear direction) is formed at a center portion of the curved portion 16. The first insertion hole 28 is a hole for introducing the medical tube 80 into a tube disposing space 30 between the fixed portion 12 and the movable portion 14, and is formed with a dimension in a width direction and a dimension in an up-down direction that allow the medical tube 80 to be inserted. A pair of column portions 32 are formed on both side portions of the first insertion hole 28, respectively. A hardness (e.g., a spring constant) during elastic deformation of the curved portion 16 is determined by the column portions 32. In some embodiments, the curved portion 16 may correspond to a living or integral hinge formed in the material of the clamp 10.

An upper end of the curved portion 16 is integrally connected to a rear end of the movable portion 14. When the curved portion 16 is elastically deformed, the movable portion 14 pivots about a rear end of the curved portion 16, and the movable portion 14 can be displaced in an up-down direction of the fixed portion 12.

Figure 3A:
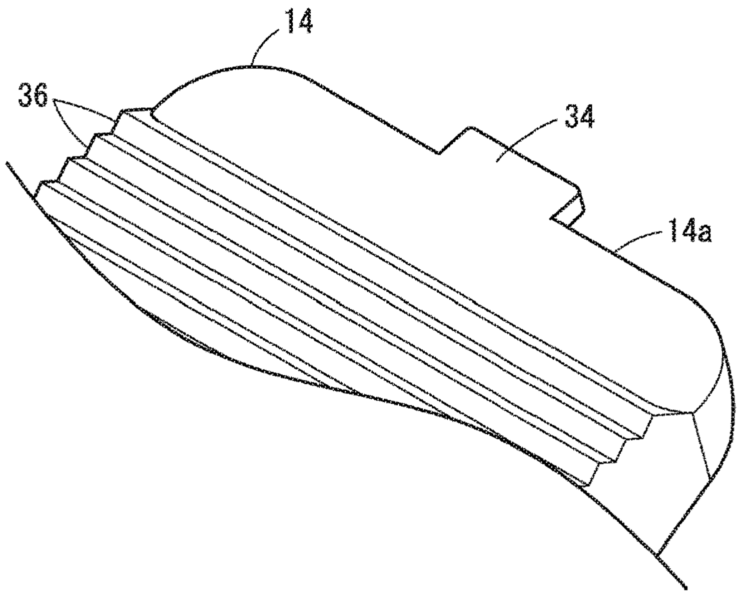
FIG. 3A is an enlarged perspective view of the vicinity of a tip of a movable portion of the clamp as shown in FIG. 1.

The movable portion 14 is a plate-like member, and includes a tip portion 14*a* disposed above a front end of the fixed portion 12. The tip portion 14*a* of the movable portion 14 is formed with a surface that stands substantially perpendicularly to an upper surface of the movable portion 14, and is formed to extend in a width direction of the movable portion 14. The tip portion 14*a* is provided with a guide protrusion 34 (e.g., a tab) constituting a part of the lateral displacement prevention mechanism 21. As illustrated in FIG. 3A, the guide protrusion 34 is formed over a range of a predetermined width from a center portion in a width direction of the tip portion 14*a*, and protrudes a short distance toward a tip side (a front side) relative to the tip portion 14*a*. As illustrated in FIG. 1, a sliding surface 14*b* obtained by obliquely cutting out a lower side of the tip portion 14*a* is formed on the lower side of the tip portion 14*a*. The sliding surface 14*b* is a surface that first comes into contact with an inclined portion 42 (described later) of the standing portion 18 and slides when the movable portion 14 is pressed.

Figure 2:
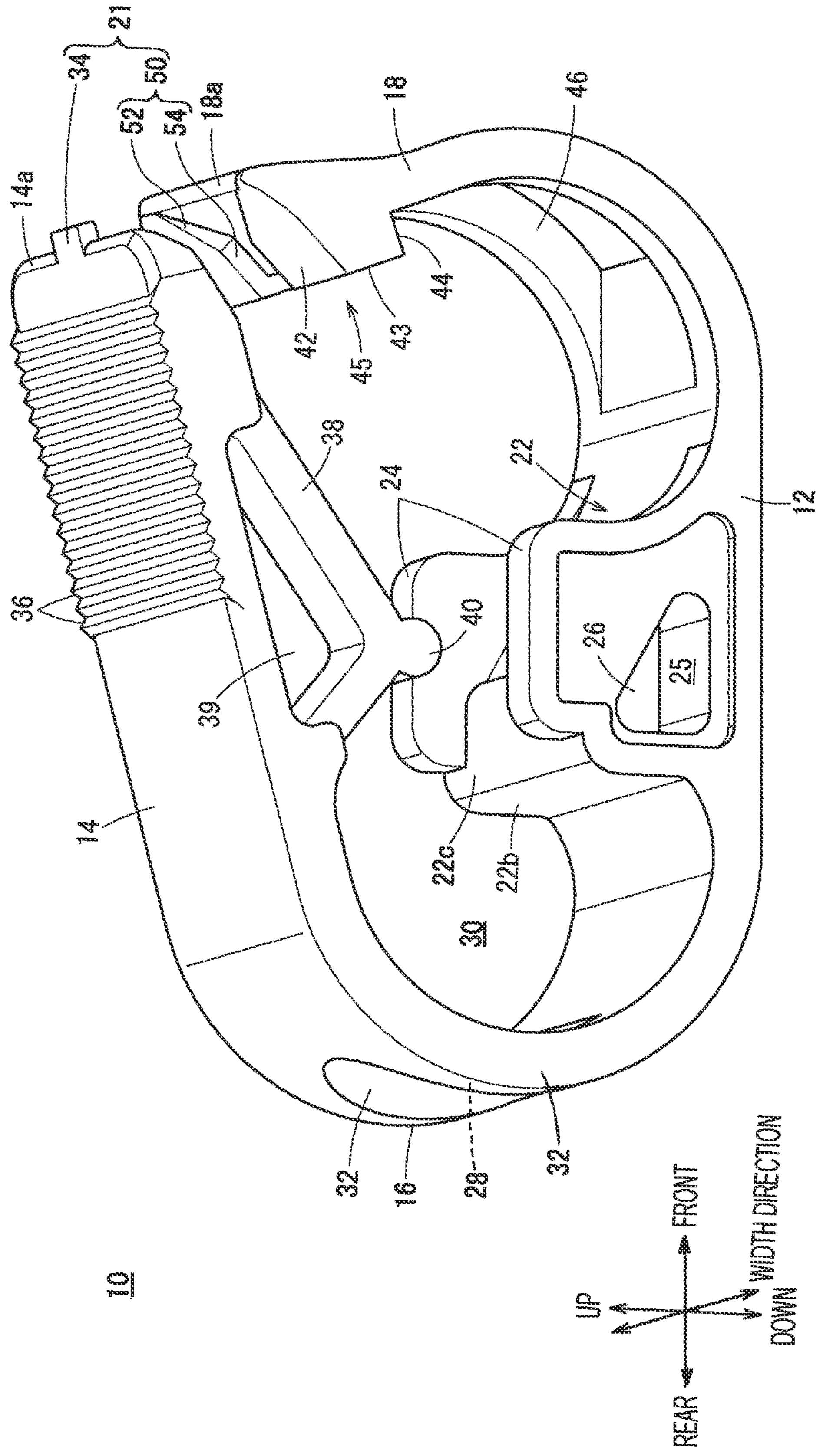
FIG. 2 is a second perspective view of the clamp according to at least one embodiment of the present disclosure.

As illustrated in FIG. 2, a plurality of ridge portions 36 formed of linear protrusions extending in the width direction are provided on the upper surface of the movable portion 14. These ridge portions 36 function as anti-slip portions when a user inputs an operation force (e.g., a pressing force, etc.) to the movable portion 14.

On a lower side of the movable portion 14, a protrusion 38 and a pressing portion 40 constituting a part of the closing portion 20 are formed. The protrusion 38 and the pressing portion 40 will be described later together with the closing portion 20.

The standing portion 18 extends from the front end of the fixed portion 12 toward the upper side of the fixed portion 12. The standing portion 18 extends toward the upper side while being curved in an arc shape in a side view, and has an upper end formed with an upper end portion 18*a* extending in a width direction. A lock mechanism 45 formed like a barb of a fish hook is formed near the upper end portion 18*a*. The lock mechanism 45 includes an inclined portion 42 inclined obliquely downward toward a rear of the clamp 10 (e.g., angling downward and rearward from a rear portion of the upper end portion 18*a*). The lock mechanism 45 may include a hanging portion 43 standing and extending downward from a lower end of the inclined portion 42, and may include a lock recess 44 extending forward (e.g., toward the front of the clamp 10) from a lower end of the hanging portion 43.

The inclined portion 42 is formed as a surface inclined downward toward the rear of the clamp 10. When the movable portion 14 is pressed, the inclined portion 42 comes into contact with the sliding surface 14*b* of the movable portion 14 causing the sliding surface 14*b* to slide, and guide the tip portion 14*a* of the movable portion 14 to engage with the lock recess 44. In addition, when a pressing force from the movable portion 14 acts on the inclined portion 42, the standing portion 18 is curved (e.g., outwardly from a center of the clamp 10, etc.) so as to be pressed and expanded forward. For instance, as the movable portion slides on the inclined portion 42, the standing portion may be elastically displaced in a direction toward the front of the clamp 10 until the tip portion 14*a* engages with the lock recess 44, at which point the standing portion may move back along a direction toward the rear of the clamp 10 locking the movable portion 14 in place.

The hanging portion 43 is formed to extend downward from the lower end of the inclined portion 42. The hanging portion 43 comes into contact with the tip portion 14*a* of the movable portion 14 to guide the tip portion 14*a* to the lock recess 44.

The lock recess 44 is formed as a groove-shaped recess extending in the width direction, and engages with the tip portion 14*a* of the movable portion 14 to prevent the movable portion 14 from returning upward and to lock the movable portion 14 in a state of being pressed downward (e.g., a pressed state).

Figure 3B:
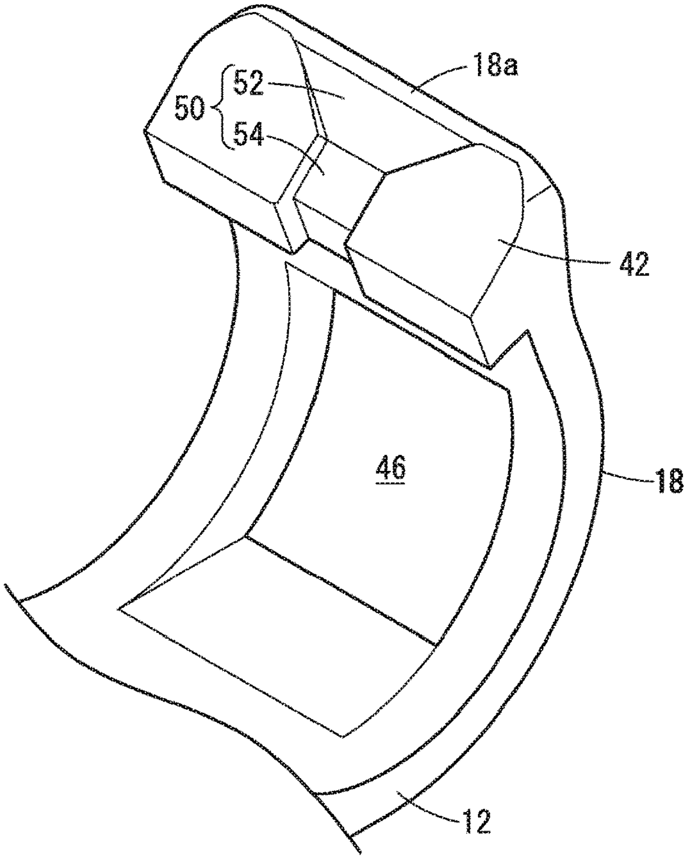
FIG. 3B is an enlarged perspective view of a standing portion of the clamp as shown in FIG. 1.

In addition, the lock mechanism 45 according to at least one embodiment of the present disclosure is formed with a guide groove 50 constituting a part of the lateral displacement prevention mechanism 21. As illustrated in FIG. 3B, the guide groove 50 is formed in a range from an upper end of the inclined portion 42 to the lower end of the hanging portion 43, and is formed along centers in width directions of the inclined portion 42 and the hanging portion 43. The guide groove 50 includes a tapered portion 52 formed in a tapered shape such that a width thereof gradually decreases from an upper end side toward the lower end side of the inclined portion 42. The guide groove 50 includes a linear portion 54 extending from a lower end of the tapered portion 52 toward the lower ends of the inclined portion 42 and the hanging portion 43. In some embodiments, the linear portion 54 may comprise a constant width that is sized slightly larger than a width of the guide protrusion 34. In some embodiments, the linear portion 54 may comprise a depth that is sized larger than a protrusion dimension (e.g., a tab height, etc.) of the guide protrusion 34. As the movable portion 14 moves between an open state and a closed state (e.g., where the movable portion 14 is locked by the lock recess 44, etc.), the tapered portion 52 catches the guide protrusion 34 and guides the guide protrusion 34 to the linear portion 54. Then, the guide protrusion 34 moves along the linear portion 54 so as to prevent the lateral displacement of the movable portion 14 when the movable portion 14 is pressed. Stated another way, when the movable portion 14 comes into contact with, and slides along, the inclined portion 42, the tapered portion 52 may contact portions of the guide protrusion 34 causing the movable portion 14 to center relative to the fixed portion 12 of the clamp 10. Once centered, further movement of the movable portion 14 relative to the fixed portion 12 of the clamp 10 causes the guide protrusion 34 to be controlled within the width of the linear portion 54. In this arrangement, any lateral misalignment between the movable portion 14 and the fixed portion 12 when moving between the open state and the closed state is corrected by the self-centering effect of the tapered portion 52 and the linear portion 54 interacting with the guide protrusion 34. Among other things, this arrangement prevents misalignment between the movable portion 14 and the fixed portion 12, when moved into the closed state and ensures reliable closing of the clamp 10 (e.g., and ensures the closure of any medical tube 80 to which the clamp 10 is attached).

A second insertion hole 46 is formed below the lock mechanism 45 of the standing portion 18. The second insertion hole 46 penetrates the standing portion 18 in a thickness direction (e.g., the front-rear direction). The second insertion hole 46 is formed in a rectangular shape when viewed from the front side. A dimension in a width direction and a dimension in an up-down direction of the second insertion hole 46 are formed to be larger than a diameter of the medical tube 80, so that the medical tube 80 can be inserted therein.

As illustrated in FIG. 1, the medical tube 80 is introduced into the tube disposing space 30 between the fixed portion 12 and the movable portion 14 through the first insertion hole 28 of the curved portion 16 and the second insertion hole 46 of the standing portion 18. Then, the medical tube 80 is closed by the closing portion 20.

As illustrated in FIG. 1, the closing portion 20 includes the base portion 22 and the sidewalls 24 formed on a fixed portion 12 side, and the protrusion 38 and the pressing portion 40 formed on a movable portion 14 side.

Among these, the base portion 22 has a gently inclined front surface 22*a*, and a rear surface 22*b* standing substantially perpendicularly to the fixed portion 12 and an upper end surface 22*c* formed between upper ends of the front surface 22*a* and the rear surface 22*b* and parallel to the fixed portion 12 as illustrated in FIG. 2. The upper end surface 22*c* is formed at a position where the upper end surface 22*c* can come into contact with the pressing portion 40 to be described later when the movable portion 14 is pressed, and is a portion that supports the medical tube 80 from below. Both side portions of the base portion 22 are lightened by a lightening portion 25. The base portion 22 is supported from below by a rib 26 provided at a center in the width direction.

The pair of sidewalls 24 are provided on both side portions of the base portion 22, respectively. Each sidewall 24 is formed to extend in a wall shape above the fixed portion 12 along a side portion of the fixed portion 12. The sidewall 24 protrudes upward relative to the upper end surface 22*c* to prevent lateral displacement of the medical tube 80.

The protrusion 38 is formed to protrude from a lower surface side of movable portion 14 toward the fixed portion 12. The protrusion 38 is formed in a triangular shape having a top portion on a lower end side in a side view. The protrusion 38 has a dimension in the width direction smaller than a distance between the pair of sidewalls 24, and can be inserted between the sidewalls 24. Both side portions of the protrusion 38 are lightened by a lightening portion 37 (e.g., recessed portion, etc.). In addition, the protrusion 38 is supported from the upper movable portion 14 side by a rib 39, or web, provided at a center of the clamp 10 in the width direction. The pressing portion 40 is formed at a lower end of the protrusion 38.

The pressing portion 40 is disposed above the vicinity of the upper end surface 22*c* of the base portion 22 and is provided to protrude from the lower end of the protrusion 38. The pressing portion 40 is formed in a columnar shape (e.g., a bar, a cylinder, curved member, etc.) having a central axis in the width direction, and presses and closes the medical tube 80 by a linear contact portion 40*a* (e.g., line contact portion) extending in the width direction. In order to enable the pressing portion 40 to be inserted between the pair of sidewalls 24, the pressing portion 40 is formed with a dimension in the width direction smaller than a gap (a separation distance in the width direction) between the pair of sidewalls 24.

The clamp 10 according to at least some embodiments of the present disclosure is implemented as described above, and some effects thereof will be described below.

Figure 4:
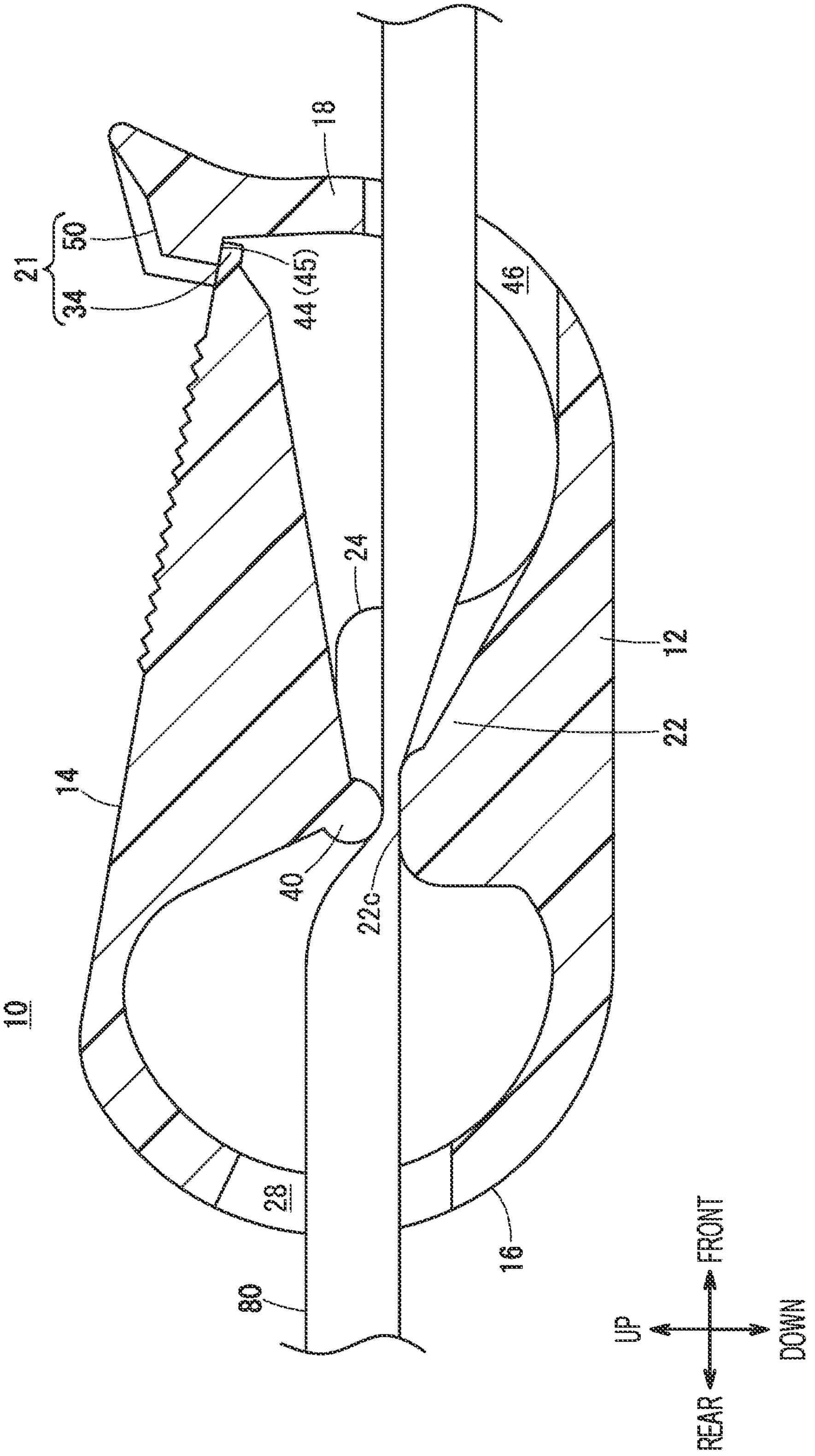
FIG. 4 is a cross-sectional view of the clamp in FIG. 1 in a closed state in accordance with embodiments of the present disclosure.

As illustrated in FIG. 4, the clamp 10 is used with the medical tube 80 inserted through the first insertion hole 28 and the second insertion hole 46. The medical tube 80 is disposed between the fixed portion 12 and the movable portion 14 and between the pair of sidewalls 24, and is held in the tube disposing space 30.

When the user presses the tip portion 14*a* of the movable portion 14 to approach the fixed portion 12 side of the clamp 10, the curved portion 16 is elastically deformed to decrease the radius of curvature of the curved portion 16. Then, the movable portion 14 is displaced to approach the fixed portion 12. The medical tube 80 is pressed while being sandwiched between the pressing portion 40 and the upper end surface 22*c* of the base portion 22. When the movable portion 14 is further pressed, the tip portion 14*a* of the movable portion 14, illustrated in FIG. 1, slides while contacting the inclined portion 42 of the standing portion 18. As the movable portion 14 is pressed down, a load in a direction of tilting the standing portion 18 forward acts via the inclined portion 42, and the upper end of the standing portion 18 is deformed to incline forward. Then, the guide protrusion 34 of the movable portion 14 is hooked onto the lock recess 44 of the standing portion 18, so that the movable portion 14 is fixed to, or locked with, the lock recess 44.

In the clamp 10, since the first insertion hole 28 through which the medical tube 80 is inserted is formed in the curved portion 16, a rigidity of the curved portion 16 is low. Therefore, when the user performs an operation of pressing the movable portion 14, the tip portion 14*a* may be displaced in the width direction, and the pressing portion 40 of the movable portion 14 may ride on the sidewalls 24.

Figure 5:
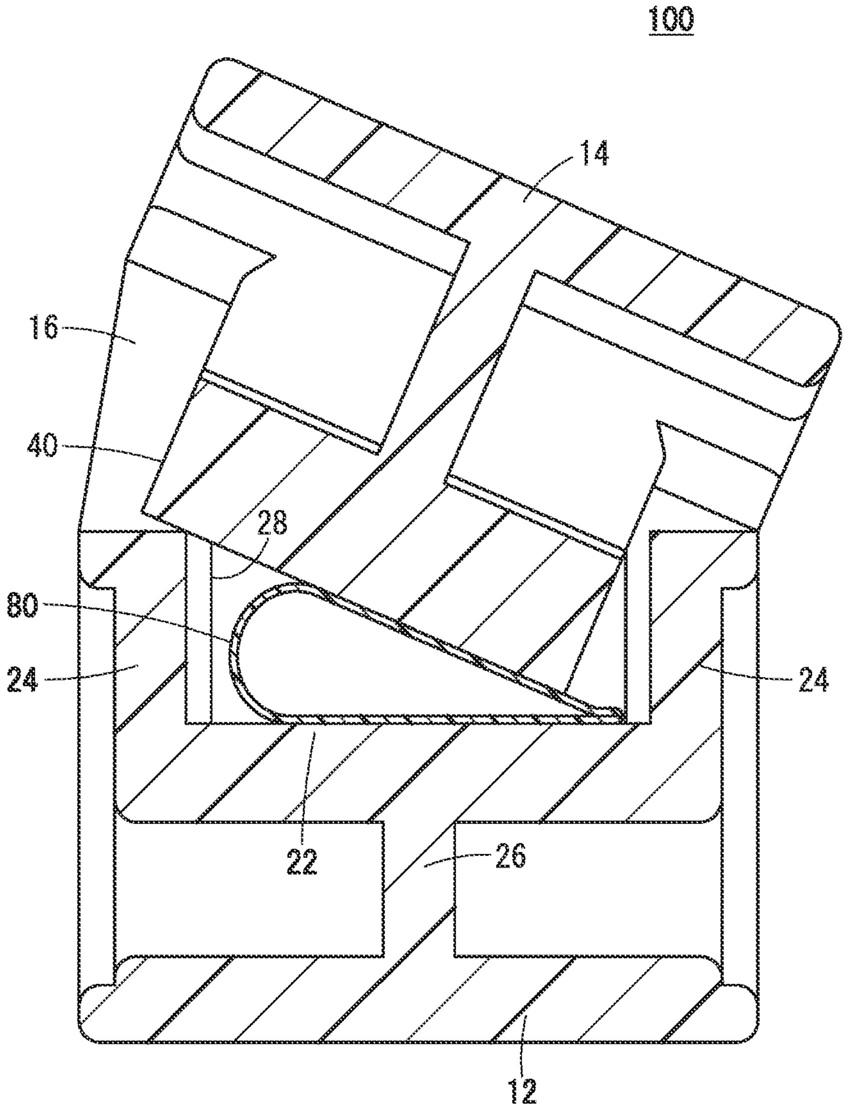
FIG. 5 is a cross-sectional view of a clamp according to a comparative example.

A clamp 100 according to a comparative example is illustrated in FIG. 5 showing an example in which the lateral displacement prevention mechanism 21 is not provided at the tip portion 14*a* of the movable portion 14 or the standing portion 18. In the clamp 100 according to the comparative example, when the pressing portion 40 rides on the sidewalls 24, this state is maintained. Even in such a case, the movable portion 14 is formed of a resin material that is easily elastically deformed, and thus in the clamp 100 according to the comparative example, the tip portion 14*a* of the movable portion 14 is fixed to the lock recess 44 while the pressing portion 40 rides on the sidewalls 24. In this comparative example, even though the clamp 100 is locked, the medical tube 80 is not completely closed. As can be appreciated, this comparative example clamp 100 would still allow fluid to flow through the medical tube 80, even though the comparative example clamp 100 is locked. When used in scenarios where drugs may be administered via the medical tube 80, bodily fluids are flowing through the medical tube 80, and/or the restriction of fluid flow is required to be accurately controlled, an operation of the comparative example clamp 100 may fail, without detection, proving to be unreliable.

In contrast, the clamp 10 according to embodiments of the present disclosure includes the lateral displacement prevention mechanism 21 including the guide protrusion 34 protruding from the tip portion 14*a* of the movable portion 14 and the guide groove 50 of the standing portion 18. When the movable portion 14 is pressed, the sliding surface 14*b* slides while contacting with the inclined portion 42 of the standing portion 18. In addition, the guide protrusion 34 of the movable portion 14 enters into the tapered portion 52 of the guide groove 50. The tapered portion 52 is formed to widen in an upper end side, and thus catch the guide protrusion 34 even when the movable portion 14 is laterally displaced.

Then, the guide protrusion 34 moves downward while engaging with the tapered portion 52, so that the guide protrusion 34 is guided to the linear portion 54, and the lateral displacement of the movable portion 14 is corrected (e.g., self-centering the movable portion 14 relative to the fixed portion 12 of the clamp 10). Thereafter, the guide protrusion 34 slides while engaging with the linear portion 54, so that the movable portion 14 is shifted without being laterally displaced. As a result, as illustrated in FIG. 4, the pressing portion 40 of the movable portion 14 is smoothly inserted into the gap between the pair of sidewalls 24 without riding on the sidewalls 24. Accordingly, the clamp 10 according to the present disclosure can reliably close the medical tube 80.

In some embodiments, the clamp 10 of the present disclosure has the following effects.

The clamp 10 according to the present disclosure includes: the fixed portion 12 including the upper portion on which the medical tube 80 (e.g., a tube) is to be placed; the movable portion 14 that faces the fixed portion 12 and is above the fixed portion 12; the curved portion 16 that is curved from one end of the fixed portion 12, extends upward, is connected to one end of the movable portion 14, and supports the movable portion 14 so as to make the movable portion 14 displaceable in the up-down direction of the fixed portion 12 with elastic deformation; the pressing portion 40 that protrudes from the movable portion 14 toward the fixed portion 12, and presses and closes the medical tube 80 when the movable portion 14 is pressed; the pair of sidewalls 24 that protrude from both side portions of the fixed portion 12 in a wall shape, respectively, and are configured to prevent the lateral displacement of the medical tube 80; and the standing portion 18 that extends upward from the other end of the fixed portion 12, faces the curved portion 16, and is provided with the lock mechanism 45 configured to maintain the movable portion 14 in the pressed state. The standing portion 18 includes the lateral displacement prevention mechanism 21 that prevents sideward deformation of the movable portion 14 when the movable portion 14 is pressed.

According to the above configuration, it is possible to prevent the lateral displacement, or misalignment, of the movable portion 14 relative to the fixed portion 12 (e.g., due to an insufficient rigidity of the curved portion 16, unequal elasticity of the side portions of the curved portion 16, a misapplied pressing force, etc.), prevent the pressing portion 40 from riding on the sidewalls 24, and to reliably close the medical tube 80 by the pressing portion 40.

In the above clamp 10, the standing portion 18 may include the lock mechanism 45 that maintains the movable portion 14 in the pressed (e.g., closed) state, and the lateral displacement prevention mechanism 21 may be implemented as an uneven structure in the lock mechanism 45. In the clamp 10, the standing portion 18 may include the inclined portion 42 configured to guide the movable portion 14 to an inner side of the standing portion 18 while sliding with the tip portion 14*a* of the movable portion 14, and the lock recess 44 formed at a lower end portion of the inclined portion 42, and the lateral displacement prevention mechanism 21 may include an uneven structure provided in the inclined portion 42.

According to the above configuration, the lateral displacement of the movable portion 14 can be prevented by the uneven structure.

The above clamp 10 may include the guide protrusion 34 that is provided at a tip of the movable portion 14 and is configured to slide while engaging with the uneven structure of the standing portion 18. In addition, in the clamp 10, the lateral displacement prevention mechanism 21 may have the guide groove 50 formed to extend downward from the upper end of the inclined portion 42 along a moving direction of the movable portion 14. According to this configuration, the lateral displacement of the movable portion 14 can be prevented with a simple structure.

In the clamp 10 configured as described above, the guide groove 50 may include the tapered portion 52 formed on an upper side and having a width gradually decreasing from the upper end side toward a lower side, and the linear portion 54 extending from the lower end of the tapered portion 52 to the lock recess 44 with a constant width. According to this configuration, even when the movable portion 14 is laterally displaced, the guide protrusion 34 can be guided to the guide groove 50 by the tapered portion 52, and the lateral displacement of the movable portion 14 can be prevented.

Figure 6A:
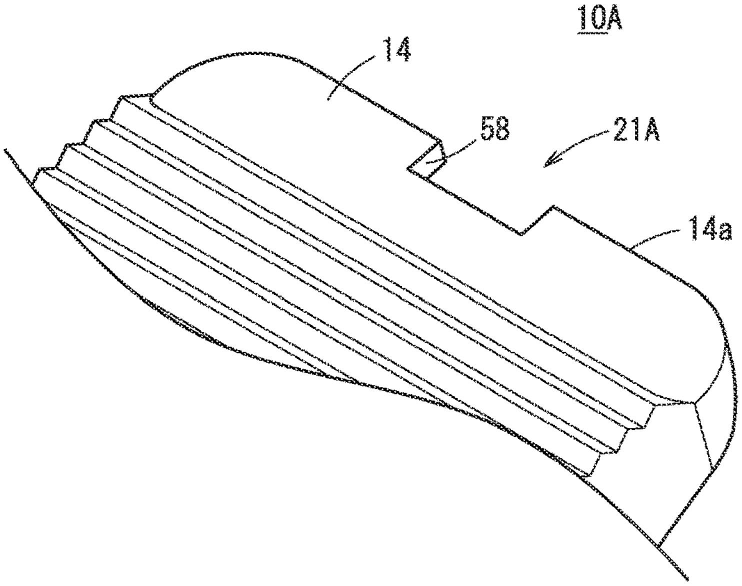
FIG. 6A is an enlarged perspective view of the vicinity of a tip of a movable portion of a clamp according to at least one embodiment of the present disclosure.
Figure 6B:
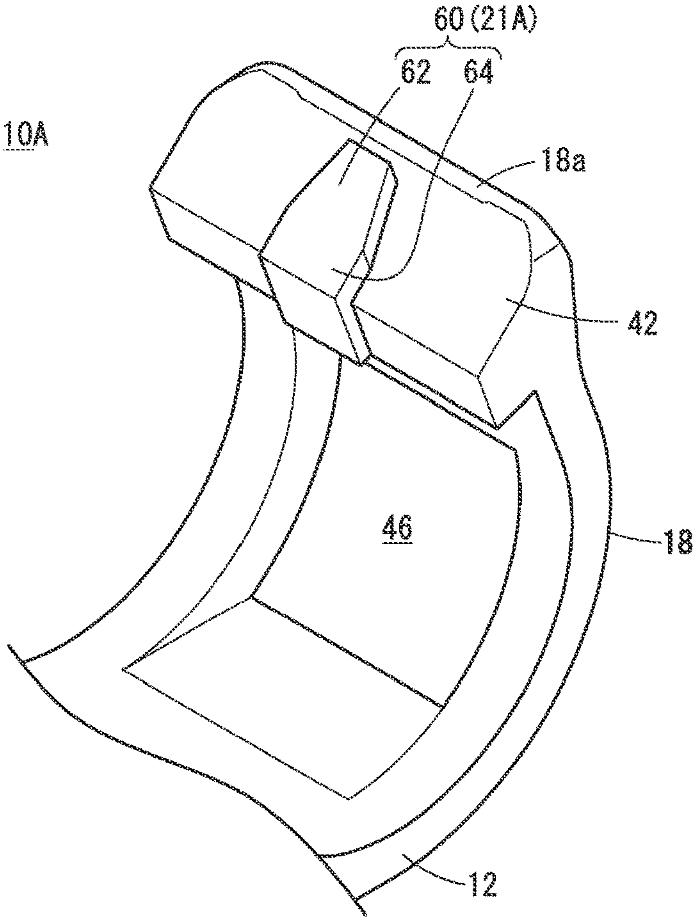
FIG. 6B is an enlarged perspective view of a standing portion of the clamp according to at least one embodiment of the present disclosure.

A clamp 10A according to at least one embodiment of the present disclosure and illustrated in FIGS. 6A and 6B may be different from the clamp 10 illustrated in FIG. 1 in that a lateral displacement prevention mechanism 21A may be provided on the tip portion 14*a* of the movable portion 14 and the lock mechanism 45 of the standing portion 18. Note that in the clamp 10A, the same components as those described in conjunction with the clamp 10 are denoted by the same reference numerals, and the detailed description thereof will be omitted.

The clamp 10A has a guide recess 58 provided on the tip portion 14*a* of the movable portion 14. The guide recess 58 is formed at a center of the movable portion 14 in the width direction of the movable portion 14 and the clamp 10. In addition, the lock mechanism 45 of the standing portion 18 of the clamp 10A is provided with a rail-shaped protrusion 60 extending from the upper end of the inclined portion 42 to the lower end of the hanging portion 43. The rail-shaped protrusion 60 is formed along a center in the width direction of the standing portion 18.

An upper portion of the rail-shaped protrusion 60 includes a tapered portion 62 having a width gradually increasing from an upper end toward a lower end, and a linear portion 64 extending downward from the lower end of the tapered portion 62 with a constant width. A width of the upper end of the tapered portion 62 is formed smaller than a width of the guide recess 58. Accordingly, even when the movable portion 14 is laterally displaced in the clamp 10A, the rail-shaped protrusion 60 can enter into the guide recess 58. The linear portion 64 of the rail-shaped protrusion 60 is formed with a width slightly smaller than that of the guide recess 58, and the guide recess 58 can slide while engaging with the linear portion 64.

In some embodiments, the clamp 10A at least has the following effects.

In the clamp 10A, the lateral displacement prevention mechanism 21A includes the rail-shaped protrusion 60 formed on the standing portion 18, and the guide recess 58 formed on the tip portion 14*a* of the movable portion 14 and slidable while engaging with the rail-shaped protrusion 60. According to this configuration, and similar to the clamp 10, it is possible to prevent the lateral displacement of the movable portion 14 during pressing, and to reliably close the medical tube 80 by the pressing portion 40 (e.g., by the pressing portion 40 remaining centered between the sidewalls 24 as the movable portion 14 moves from an open state of the clamp 10A to a closed state of the clamp 10A.

Figure 7A:
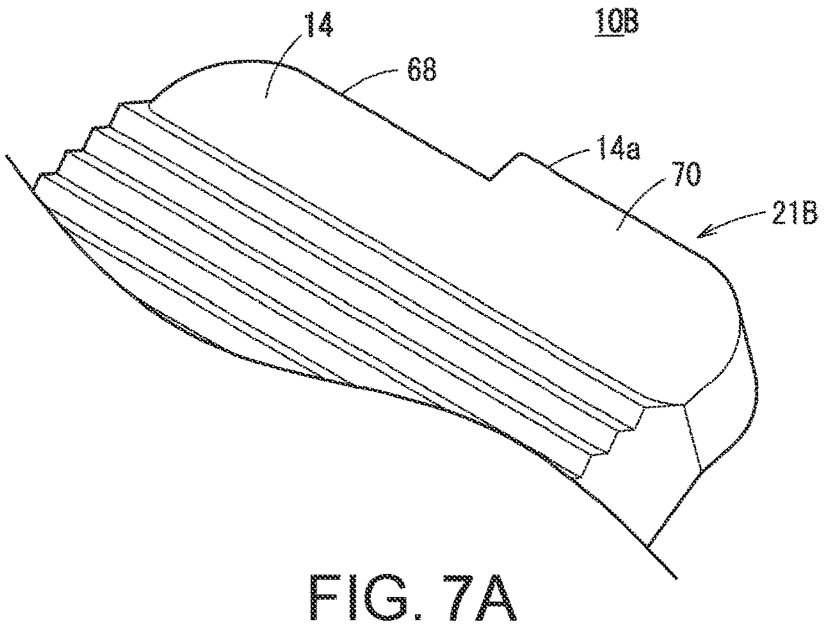
FIG. 7A is an enlarged perspective view of the vicinity of a tip of a movable portion of a clamp according to at least one embodiment of the present disclosure.
Figure 7B:
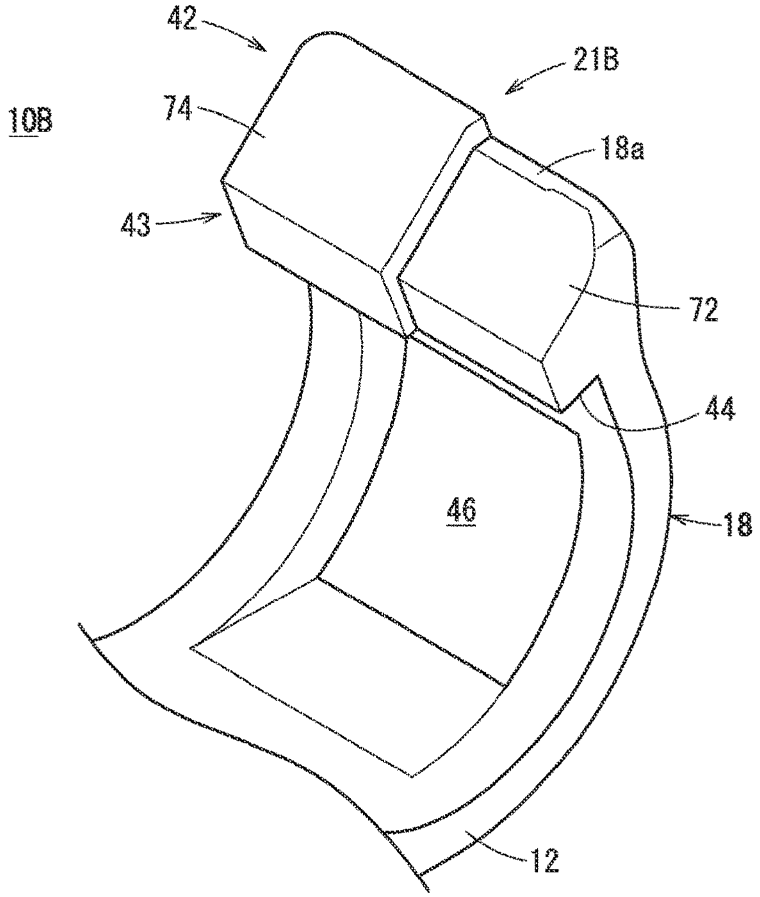
FIG. 7B is an enlarged perspective view of a standing portion of a clamp according to at least one embodiment of the present disclosure.

A clamp 10B according to at least one embodiment of the present disclosure is illustrated in FIGS. 7A and 7B. The clamp 10B may be different from the clamp 10 (illustrated in FIG. 1) in that a lateral displacement prevention mechanism 21B may be provided on the tip portion 14*a* of the movable portion 14 and the lock mechanism 45 of the standing portion 18. Unlike the clamp 10 and 10A, the clamp 10B may not be symmetrical about a plane running through a width center of the clamp 10B (e.g., running from the front of the clamp 10B to the rear of the clamp 10B). Note that in the clamp 10B, the same components as those described in conjunction with the clamp 10 are denoted by the same reference numerals, and the detailed description thereof will be omitted.

As illustrated in FIG. 7A, the clamp 10B includes a recess 68 and a protrusion 70 constituting a part of the lateral displacement prevention mechanism 21B at the tip portion 14*a* of the movable portion 14. The recess 68 is formed on one side (a back side in the drawing) from the center in the width direction of the movable portion 14, and the protrusion 70 is formed on the other side (a front side in the drawing) from the center in the width direction of the movable portion 14. As illustrated in FIG. 7A, the protrusion 70 protrudes a short distance in a tip direction of the tip portion 14*a*.

In addition, and as illustrated in FIG. 7B, in the clamp 10B, a recess 72 and a protrusion 74 are formed over the inclined portion 42 and the hanging portion 43 of the standing portion 18. The recess 72 of the standing portion 18 is formed on the other side (the front side in the drawing) from the center in the width direction of the standing portion 18 and on a portion corresponding to the protrusion 70 of the movable portion 14. In addition, the protrusion 74 of the standing portion 18 is formed on the one side (the back side in the drawing) from the center in the width direction of the standing portion 18 and on a portion corresponding to the recess 68 of the movable portion 14. A boundary between the recess 72 and the protrusion 74 of the standing portion 18 extends in a planar shape along a center line in the width direction of the standing portion 18.

In the clamp 10B, when the movable portion 14 is pressed toward the fixed portion 12, the tip portion 14*a* of the movable portion 14 comes into contact with the inclined portion 42 of the standing portion 18. Then, the protrusion 70 of the tip portion 14*a* engages with the recess 72 of the inclined portion 42, and the recess 68 of the tip portion 14*a* engages with the protrusion 74 of the inclined portion 42. Then, these protrusions and recesses slide while engaging with each other. When the user presses the movable portion 14 while applying a slight force so as to press the protrusion 70 of the movable portion 14 against the recess 72 of the standing portion 18, a center position in the width direction of the movable portion 14 is kept in a state of coinciding with a center position in the width direction of the fixed portion 12. When the user presses the movable portion 14 toward the fixed portion 12, the medical tube 80 can be closed while preventing the lateral displacement of the movable portion 14.

Although the present disclosure has been described above with reference to preferred embodiments, the present disclosure is not limited to the above embodiments, and it goes without saying that various modifications can be made without departing from the gist of the present disclosure.

References in the specification to "one embodiment," "an embodiment," "an example embodiment," "some embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in conjunction with one embodiment, it is submitted that the description of such feature, structure, or characteristic may apply to any other embodiment unless so stated and/or except as will be readily apparent to one skilled in the art from the description. The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

It is to be appreciated that any feature described herein can be claimed in combination with any other feature(s) as described herein, regardless of whether the features come from the same described embodiment.

As used herein, the singular forms "a," "an," and "the" are intended to include the plural forms as well, unless the context clearly indicates otherwise. It will be further understood that the terms "include," "including," "includes," "comprise," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. The term "and/or" includes any and all combinations of one or more of the associated listed items.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B, and C together. When each one of A, B, and C in the above expressions refers to an element, such as X, Y, and Z, or a class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and this disclosure.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

What is claimed is:

1. A clamp, comprising:

a fixed portion that extends from a rear end of the fixed portion to a front end of the fixed portion, wherein the fixed portion comprises an upper portion arranged at a point between the rear end and the front end, and wherein the upper portion is arranged to receive a tube;

a curved hinge portion interconnected to the rear end of the fixed portion, wherein the curved hinge portion extends upward in a curved direction away from the fixed portion to an upper end of the curved hinge portion;

a movable portion interconnected to the upper end of the curved hinge portion at a rear end of the fixed portion, wherein the movable portion extends from the rear end of the movable portion to a tip portion of the movable portion, wherein the curved hinge portion is elastically deformable and the movable portion moves between an open state and a closed state relative to the fixed portion, and wherein the movable portion comprises:

a pressing portion that protrudes from the movable portion in a direction toward the fixed portion, the pressing portion being configured to press and close the tube when the movable portion is in the closed state; and a guide protrusion extending a distance from the tip portion in a linear direction away from the rear end of the movable portion, wherein the guide protrusion comprises an upper surface that is arranged coplanar with an upper surface of the movable portion;

a pair of sidewalls that protrude from side portions of the fixed portion in a wall shape, respectively, and are configured to prevent lateral displacement of the tube; and a standing portion that extends upward from the front end of the fixed portion and faces the curved hinge portion, wherein the standing portion comprises:

an inclined portion arranged at an angle extending obliquely downward toward the rear end of the fixed portion;

a hanging portion extending from a lower end of the inclined portion downward toward the fixed portion; and a guide groove extending a depth into the inclined portion, the guide groove comprising a tapered portion and a linear portion that is interconnected to the tapered portion, wherein the linear portion is arranged at the angle extending obliquely downward toward the rear end of the fixed portion, wherein the guide groove is configured to receive the guide protrusion in the tapered portion and then receive the guide protrusion in the linear portion as the movable portion moves from the open state to the closed state, and wherein the guide groove prevents lateral displacement of the movable portion relative to the fixed portion as the movable portion moves from the open state to the closed state.

2. The clamp of claim 1, wherein the guide groove extends a dimension into the hanging portion, and wherein the standing portion further comprises:

a lock recess formed at a lower end portion of the hanging portion.

3. The clamp of claim 2, wherein a width of the guide protrusion is less than a width of the linear portion.

4. The clamp of claim 3, wherein a width of the pressing portion is less than a dimension measured between the pair of sidewalls.

5. The clamp of claim 4, wherein the linear portion comprises a constant width extending along an entirety of the linear portion.

6. The clamp of claim 5, wherein the curved hinge portion further comprises a pair of column portions forming a first aperture through which the tube can be inserted, wherein the standing portion comprises a rectangular insertion hole forming a second aperture through which the tube can be inserted, and wherein the rectangular insertion hole is arranged entirely below the inclined portion.

7. The clamp of claim 1, wherein the upper surface of the movable portion comprises a plurality of ridge portions extending across a width of the movable portion.

8. The clamp of claim 1, wherein the pressing portion slots in between the pair of sidewalls when the movable portion is in the closed state.

9. A clamp, comprising:

a fixed portion comprising:

a pair of sidewalls that protrude from the fixed portion in a first direction to an upper surface of the pair of sidewalls; and a contact surface arranged in a space between the pair of sidewalls and disposed below the upper surface of the pair of sidewalls;

a movable portion that faces the fixed portion and disposed above the fixed portion, wherein the movable portion moves between an open state and a closed state relative to the fixed portion;

a curved portion that curves from a first end of the fixed portion to a first end of the movable portion, the curved portion supporting the movable portion such that the movable portion is displaceable in the first direction and a second direction opposite the first direction with elastic deformation;

a pressing portion interconnected with the movable portion, wherein the pressing portion extends from the movable portion in a direction toward the fixed portion, the pressing portion configured to press and close a tube disposed on the contact surface when the movable portion is in the closed state, wherein the pressing portion comprises:

a first protrusion portion interconnected to the movable portion that extends toward the fixed portion a first distance from a point adjacent the first end of the movable portion to a bar portion of the pressing portion; and a second protrusion portion interconnected to the movable portion that extends toward the fixed portion a second from a point adjacent a tip portion of the movable portion to the bar portion of the pressing portion, wherein the bar portion of the pressing portion is arranged adjacent and offset from the contact surface in the open state and in the closed state;

wherein the pressing portion slots in between the pair of sidewalls when the movable portion is in the closed state; and a guide protrusion extending from the tip portion in a direction away from the first end of the movable portion, wherein the guide protrusion comprises an upper surface arranged coplanar with an upper surface of the movable portion;

a standing portion that extends upward from a second end of the fixed portion, faces the curved portion, and comprises:

an inclined portion arranged at an angle extending obliquely downward toward the first end of the fixed portion;

a hanging portion extending from a lower end of the inclined portion downward toward the fixed portion;

a guide groove extending into the inclined portion, the guide groove comprising a tapered portion and a linear portion interconnected to the tapered portion, wherein the linear portion is arranged at the angle, wherein the guide groove is configured to receive the guide protrusion in the tapered portion and then receive the guide protrusion in the linear portion as the movable portion moves from the open state to the closed state, and wherein the guide groove prevents lateral displacement of the movable portion relative to the fixed portion as the movable portion moves from the open state to the closed state; and a lock mechanism configured to maintain the movable portion in the closed state when the tip portion of the movable portion is moved downward past the hanging portion.

10. The clamp of claim 9, wherein the inclined portion is configured to guide the movable portion to an inner side of the standing portion as the movable portion moves from the open state to the closed state.

11. The clamp of claim 9, wherein the curved portion further comprises a pair of column portions forming a first aperture through which the tube can be inserted.

12. The clamp of claim 9, wherein the movable portion comprises ridge portions disposed on an upper surface of the movable portion.

13. The clamp of claim 9, wherein the lock mechanism further comprises:

a lock recess extending from a lower end of the hanging portion toward the second end of the fixed portion.

14. The clamp of claim 13, wherein the upper surface of the guide protrusion is engaged with a portion of the lock recess.

15. The clamp of claim 9, further comprising:

a web arranged at a width center of the clamp, the web arranged in contact with the first protrusion portion, the second protrusion portion, and the movable portion, wherein the width center of the clamp is arranged between the pair of sidewalls.

16. The clamp of claim 9, wherein the standing portion is configured to deform and incline in a direction away from the first end of the fixed portion as the movable portion moves from the open state to the closed state.

17. A clamp, comprising:

a fixed portion comprises an upper portion on which a tube can be placed;

a movable portion that faces the fixed portion and is disposed above the fixed portion, comprising a sliding surface arranged at a second end of the movable portion;

a curved portion that curves from a first end of the fixed portion, extends upward, connects to a first end of the movable portion, and supports the movable portion so as to make the movable portion displaceable in an up-down direction of the fixed portion with elastic deformation;

a pressing portion that protrudes from the movable portion in a direction toward the fixed portion, and presses and closes the tube when the movable portion is pressed;

a pair of sidewalls that protrude from side portions of the fixed portion in a wall shape, respectively, and are configured to prevent lateral displacement of the tube; and a standing portion that extends upward from a second end of the fixed portion, faces the curved portion, wherein the standing portion comprises:

a lock mechanism configured to maintain the movable portion when the movable portion is in a pressed state;

an inclined portion having a surface comprising an oblique angle that is configured to contact the sliding surface and guide the movable portion to an inner side of the standing portion while interfacing with a tip of the movable portion; and a lateral displacement prevention mechanism that prevents a sideward deformation of the movable portion when the movable portion is pressed, comprising:

a guide portion having a surface extending from an upper end portion of the standing portion to a locking recess operable to receive at least a part of the movable portion, a tapered portion;

a linear portion; and a hanging portion arranged below the tapered portion and the linear portion;

wherein the surface of the guide portion is arranged in a different plane than the surface of the inclined portion, and wherein the guide portion has a first width proximal to the upper end portion which changes via the tapered portion into a second width of the linear portion that extends to the hanging portion.

18. The clamp of claim 17, wherein the surface of the guide portion is at least one of a recess and a protrusion relative to the surface of the inclined portion, and wherein a surface of the linear portion and the surface of the inclined portion are arranged parallel to one another.

19. The clamp of claim 18, wherein the recess is disposed on a first side of the inclined portion, and wherein the protrusion is disposed on a second side of the inclined portion opposite the first side.

20. The clamp of claim 19, wherein the tip of the movable portion comprises a protrusion that engages with the recess of the inclined portion, and wherein the tip of the movable portion comprises a recess that engages with the protrusion of the inclined portion.

* * * * *